United States Patent
Moon et al.

(10) Patent No.: US 9,888,929 B2
(45) Date of Patent: Feb. 13, 2018

(54) DRILL, DRILL COVER, AND SURGICAL INSTRUMENT FOR COLLECTING AUTOLOGOUS BONE EMPLOYING SAME

(75) Inventors: Jong Hoon Moon, Busan (KR); Tae Euk Lee, Busan (KR); Tae Gwan Eom, Busan (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 466 days.

(21) Appl. No.: 14/238,049

(22) PCT Filed: Aug. 13, 2012

(86) PCT No.: PCT/KR2012/006427
§ 371 (c)(1),
(2), (4) Date: Feb. 10, 2014

(87) PCT Pub. No.: WO2013/022324
PCT Pub. Date: Feb. 14, 2013

(65) Prior Publication Data
US 2014/0194881 A1  Jul. 10, 2014

(30) Foreign Application Priority Data

Aug. 11, 2011 (KR) .......................... 10-2011-0080311
Aug. 24, 2011 (KR) .......................... 10-2011-0084813

(51) Int. Cl.
*A61B 17/16* (2006.01)
*A61C 3/02* (2006.01)

(52) U.S. Cl.
CPC ...... *A61B 17/1637* (2013.01); *A61B 17/1635* (2013.01); *A61C 3/02* (2013.01)

(58) Field of Classification Search
CPC ............ A61B 17/1615; A61B 17/1637; A61B 17/1688; A61B 17/1695

(Continued)

(56) References Cited

U.S. PATENT DOCUMENTS 1,984,839 A * 12/1934 Murray ..................... G09F 3/00
116/200
3,564,947 A *  2/1971 Maier ..................... B23B 51/02
408/211

(Continued)

FOREIGN PATENT DOCUMENTS

CN       2097620 U     3/1992
EP       1105058 A1    6/2001

(Continued)

OTHER PUBLICATIONS

"ACM Bone Collector". Product Brochure [online]. NeoBiotech, Jul. 10, 2012 [retrieved on Apr. 26, 2016 from the WayBack Machine online]. Retrieved from the Internet: <URL: http://www.osseonews.com/shop/acm-bone-collector-innovative-technology-to-collect-and-harvest-cortical-bone/>.*

(Continued)

*Primary Examiner* — Tatiana Nobrega
*Assistant Examiner* — Jessica Weiss
(74) *Attorney, Agent, or Firm* — Ladas & Parry LLP

(57) ABSTRACT

A drill and drill cover and autogenous bone collector using the same are provided. The autogenous bone collector comprises a shaft unit connected to a driving device and a cutting unit which revolves and collects bone particles of a patient. The cross-sectional area of the cutting unit is from 10% to 40% of an area of a circle having a radius corresponding to a distance from the center of the cutting unit to the outermost end portion of the cutting unit.

15 Claims, 20 Drawing Sheets

(58) Field of Classification Search
USPC ....... 606/80, 84, 180; 433/165–166; 407/32, 407/42, 53–54, 61–63; 408/223–224, 408/227–230
See application file for complete search history.

(56) References Cited

U.S. PATENT DOCUMENTS

| | | | |
|---|---|---|---|
| 4,605,345 A | | 8/1986 | Giughese |
| 4,652,185 A | | 3/1987 | Malrick |
| 4,830,000 A | | 5/1989 | Shutt |
| 6,071,284 A | * | 6/2000 | Fox .................... A61B 10/0233 606/102 |
| 6,312,432 B1 | * | 11/2001 | Leppelmeier ...... A61B 17/1615 408/225 |
| 6,604,945 B1 | | 8/2003 | Jones |
| 6,764,452 B1 | | 7/2004 | Gillespie et al. |
| 2002/0022847 A1 | * | 2/2002 | Ray, III ............... A61B 17/025 606/96 |
| 2002/0119418 A1 | | 8/2002 | Matsutani et al. |
| 2004/0210229 A1 | * | 10/2004 | Meller ................. A61B 10/025 606/80 |
| 2006/0008771 A1 | | 1/2006 | Courvoisier |
| 2006/0111724 A1 | | 5/2006 | Yeung Wai Ping |
| 2009/0047085 A1 | * | 2/2009 | Liao ...................... B27G 15/00 408/230 |
| 2009/0080989 A1 | * | 3/2009 | Dost ...................... B23B 51/02 408/225 |
| 2009/0142731 A1 | | 6/2009 | Kim |
| 2010/0196844 A1 | | 8/2010 | Heb |
| 2011/0223558 A1 | * | 9/2011 | Anitua Aldecoa ... A61C 8/0089 433/141 |

FOREIGN PATENT DOCUMENTS

| | | | |
|---|---|---|---|
| EP | 2138255 A2 | | 12/2009 |
| JP | 06-304187 A | | 11/1994 |
| JP | 10-118085 A | | 5/1998 |
| JP | 11-514905 A | | 12/1999 |
| JP | 2002-253578 A | | 9/2002 |
| JP | 2008-188037 A | | 8/2008 |
| JP | 2009-131634 A | | 6/2009 |
| JP | 2009-261254 A | | 11/2009 |
| KR | 20-0406694 Y1 | | 1/2006 |
| KR | 1020070108777 A | | 11/2007 |
| KR | 10-0796907 B1 | | 1/2008 |
| KR | 100813434 B1 | | 3/2008 |
| KR | 100838942 B1 | | 6/2008 |
| KR | 101013285 B1 | | 2/2011 |
| KR | 1020110016602 A | | 2/2011 |
| KR | 10-1247516 | * 11/2012 | ............. A61B 17/16 |
| TW | M353727 | * 7/1997 | |
| TW | 568765 B | | 1/2004 |
| TW | 353727 U | | 4/2009 |
| WO | 9716118 A1 | | 5/1997 |

OTHER PUBLICATIONS

Extended European Search Report Appln. No. 12821622.3-1654: dated Jan. 7, 2015.
Taiwan First Office Action dated Jul. 17, 2014; Appln. No. 101129224.
Japanese Office Action dated Feb. 17, 2015; Appln. No. 2014-524947.
Korean Patent Office Notice of Allowance dated Mar. 7, 2012 Appln. No. 10-2011-0080311.
Korean Patent Office Notice of Allowance dated Mar. 7, 2012 Appln. No. 10-2011-0084813.
International Search Report dated Jan. 23, 2013; PCT/KR2012/006427.
Japanese Office Action Appln. No. 2014-524947; dated Oct. 6, 2015.
Chinese Office Action dated Mar. 21, 2016; Appln. No. 201280039246.9.
Second Chinese Office Action dated Nov. 22, 2016; Appln. 201280039246.9.

* cited by examiner

DRILL, DRILL COVER, AND SURGICAL INSTRUMENT FOR COLLECTING AUTOLOGOUS BONE EMPLOYING SAME

TECHNICAL FIELD

The present invention relates to a drill, a drill cover, and an autogenous bone collector using the same, and more particularly, to a drill and a drill cover for collecting bone particles during an implant surgery, improving a capacity of housing bone particles, easily separating collected bone particles from a cutting unit, controlling depth of the cutting unit penetrating into an autogenous bone, and for housing bone particles collected by the drill within the drill cover without popping out of the drill cover, and an autogenous bone collector using the same.

BACKGROUND ART

During an implant surgery, a method of collecting bone particles of a patient and implanting the same is used. The bone particles are collected from an autogenous bone of a patient by using a drill attached to a dental hand piece. Korean Utility Model Registration No. 20-0406694 that was registered on Jan. 13, 2006 prior to this application discloses such an autogenous bone collecting device.

However, the conventional autogenous bone collecting device has inconvenience of removing bone particles that are stuck at threads of a drill during collection of bone particles of a patient.

DETAILED DESCRIPTION OF THE INVENTION

Technical Problem

The present invention provides a drill and a drill cover for improving a capacity of housing bone particles, easily separating bone particles from a cutting unit, controlling depth of the cutting unit penetrating into an autogenous bone, and for housing bone particles collected by the drill within the drill cover without popping out of the drill cover, and an autogenous bone collector using the same.

Advantageous Effects

According to embodiments of the present invention as described above, there are provided a drill and a drill cover for collecting bone particles during an implant surgery, improving a capacity of housing bone particles, easily separating bone particles from a cutting unit, controlling depth of the cutting unit penetrating into an autogenous bone, and for housing bone particles collected by the drill within the drill cover without popping out of the drill cover, and an autogenous bone collector using the same.

DESCRIPTION OF THE DRAWINGS

The above and other features and advantages of the present invention will become more apparent by describing in detail exemplary embodiments thereof with reference to the attached drawings in which.

BEST MODE

Figure 1:
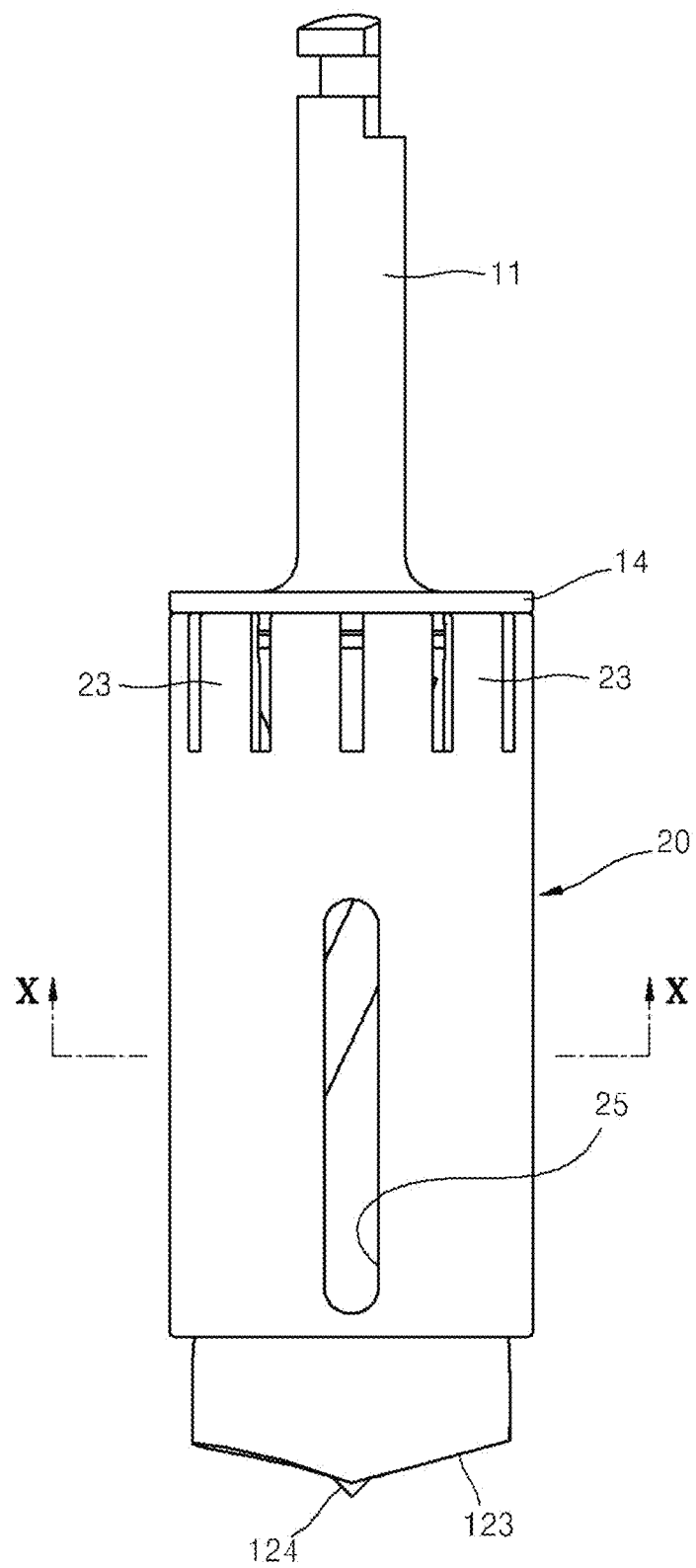
FIG. 1 is a front view of an autogenous bone collector according to an embodiment of the present invention.

According to an aspect of the present invention, there is provided a drill including a shaft unit connected to a driving device; and a cutting unit, which revolves and collects bone particles of a patient, wherein the cross-sectional area of the cutting unit is from 10% to 40% of an area of a circle having a radius corresponding to a distance from the center of the cutting unit to the outermost end portion of the cutting unit.

The end portion of the cutting unit may include a sloped surface, such that the center portion of the cutting unit has a pointed shape, and a pointer that protrudes and has a larger slope than the sloped surface may be attached to the center portion of the end portion of the cutting unit.

The cutting unit may include a first blade, which spirally extends; and a second blade, which spirally extends at a same pitch as the first blade.

The outermost thickness of the first blade or the second blade may be greater than thickness of the center portion of the first blade or the second blade.

The end portion of the cutting unit may include two or more sub-sloped surfaces on the first and second blades, having different slopes.

The thickness of the cutting unit may be constant or increases toward the shaft unit.

According to another aspect of the present invention, there is provided an autogenous bone collector including a drill having a shaft unit connected to a driving device and a cutting unit, which revolves and collects bone particles of a patient; and a drill cover, which is attached to the drill and forms a storage space between the inner circumferential surface of the drill cover and the outer circumferential surface of the cutting surface of the cutting unit for housing the collected bone particles.

The leading end portion of the drill may be capable of protruding from the drill cover, and the drill cover may include a housing portion through which passes the cutting surface of the cutting unit.

The drill may include a shoulder protruding from the outer circumferential surface of the drill, movement of the drill cover may be restricted by the shoulder, and a first protrusion may be formed below the shoulder.

A second protrusion may be formed below the first protrusion.

The autogenous bone collector may further include a partitioning wall, which extends from the inner circumferential surface of the drill cover, wherein, when the partitioning wall moves toward the leading end portion of the cutting unit, bone particles stored in the storage space may be moved toward the leading end portion.

The autogenous bone collector may further include protruding fingers formed at the upper portion of the drill cover, wherein the protruding fingers may protrude from the upper end of the drill cover to be apart from each other by a constant interval in the circumferential direction, and hook protrusions that are bent inward may be arranged at the upper ends of protruding fingers.

A long hole having a long shape and penetrating through the outer circumferential surface and the inner circumferential surface of the drill cover may be formed in the drill cover.

According to another aspect of the present invention, there is provided a drill cover, which is attached to a drill having a cutting unit for collecting bone particles of a patient during revolution, including a main body that has the top and the bottom opened and is attached to the exterior of the cutting unit, wherein the main body is compressible in a direction in which the upper portion and the lower portion of the main body approach to each other.

A cut-open portion, which includes spiral cuts, may be formed in the main body.

The cut-open portion may be formed at a constant pitch.

The cut-open portion may be formed at varying pitches.

Width of the cut-open portion may be constant.

The cut-open portion may include a first cut-open portion having a constant first cut-open width; and a second cut-open portion having a second cut-open width smaller than the first cut-open width.

The second cut-open portion may extend from the two opposite ends of the first cut-open portion, and width of the second cut-open portion may gradually decrease toward an end portion thereof.

The cut-open portion may extend downward while rotating to the left or the right in a spiral shape.

The drill cover may further include protruding fingers protruding upward from the upper end of the drill cover to be apart from each other by a constant interval in the circumferential direction.

The drill cover may further include a partitioning wall, which extends from the inner circumferential surface of the drill cover, wherein, when the partitioning wall may include a housing portion through which passes the cutting surface of the cutting unit.

Hook protrusions that are bent inward may be arranged at the upper end of main body.

The main body may be formed of titanium nitride or stainless steel.

According to another aspect of the present invention, there is provided an autogenous bone collector including a drill having a shaft unit connected to a driving device and a cutting unit, which revolves and collects bone particles of a patient; and a drill cover, includes a main body that has the top and the bottom opened and is attached to the exterior of the cutting unit, wherein the main body is compressible in a direction in which the upper portion and the lower portion of the main body approach to each other A cut-open portion, which includes spiral cuts, may be formed in the main body.

The cut-open portion may be formed at a constant pitch.

The cut-open portion may be formed at varying pitches.

Width of the cut-open portion may be constant.

The cut-open portion may include a first cut-open portion having a constant first cut-open width; and a second cut-open portion having a second cut-open width smaller than the first cut-open width.

The second cut-open portion may extend from the two opposite ends of the first cut-open portion, and width of the second cut-open portion may gradually decrease toward an end portion thereof.

The cut-open portion may extend downward while rotating to the left or the right in a spiral shape.

The autogenous bone collector may further include protruding fingers protruding upward from the upper end of the drill cover to be apart from each other by a constant interval in the circumferential direction.

The autogenous bone collector may further include a partitioning wall, which extends from the inner circumferential surface of the drill cover, wherein, when the partitioning wall may include a housing portion through which passes the cutting surface of the cutting unit.

Hook protrusions that are bent inward are arranged at the upper end of main body.

The main body may be formed of titanium nitride or stainless steel.

The cross-sectional area of the cutting unit may be from 10% to 40% of an area of a circle having a radius corresponding to a distance from the center of the cutting unit to the outermost end portion of the cutting unit.

The cutting unit may include a shoulder protruding from the outer circumferential surface of the drill, movement of a drill cover may be restricted by the shoulder, and a first protrusion may be formed below the shoulder.

A second protrusion may be formed below the first protrusion.

The cutting unit may include a first blade, which spirally extends; and a second blade, which spirally extends at a same pitch as the first blade.

The end portion of the cutting unit may include two or more sub-sloped surfaces having different slopes.

The cutting unit may include a pointer that protrudes from the center portion of the end portion of the cutting unit.

The thickness of the cutting unit may be constant or increases toward the shaft unit.

MODE OF THE INVENTION

The present invention relates to a drill and a drill cover for an autogenous bone collector and an autogenous bone collector employing the same, particularly for collecting bone particles during an implant surgery.

Hereinafter, exemplary embodiments of the present invention will be described in detail with reference to the attached drawings.

Figure 2:
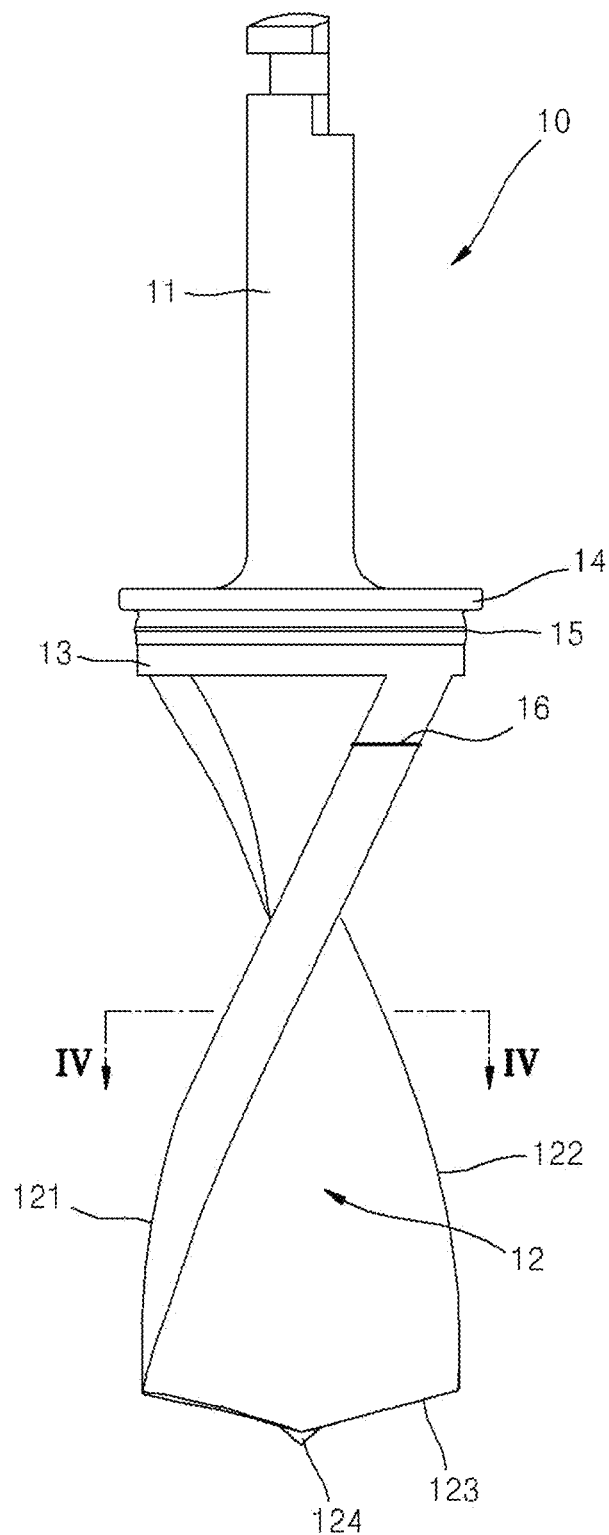
FIG. 2 is a front view of a drill employed in the autogenous bone collector shown in FIG. 1.
Figure 3:
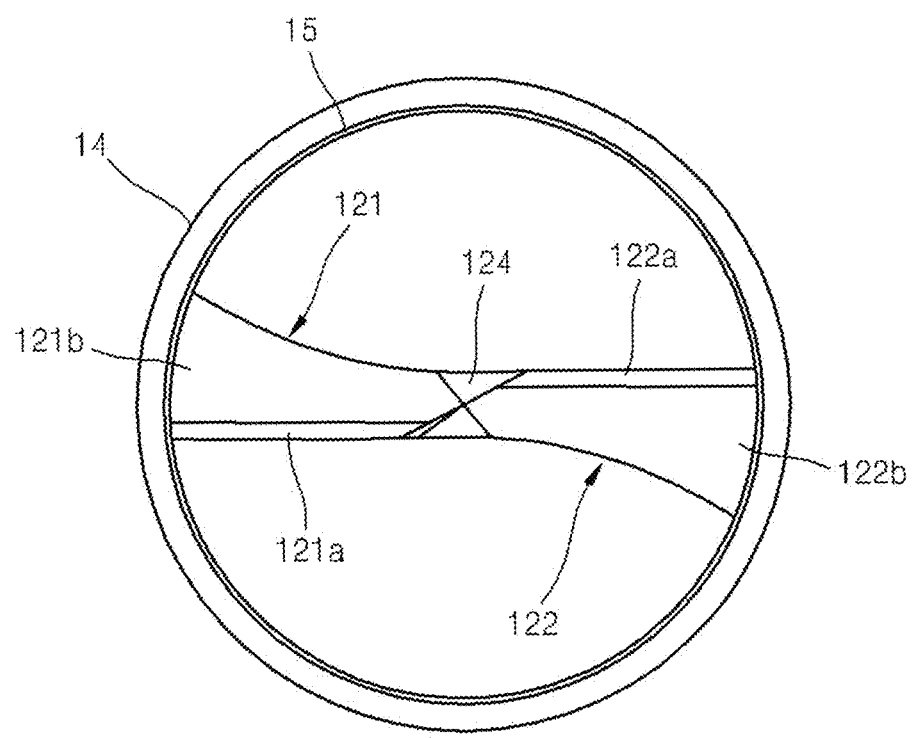
FIG. 3 is a bottom view of the drill shown in FIG. 2.
Figure 4:
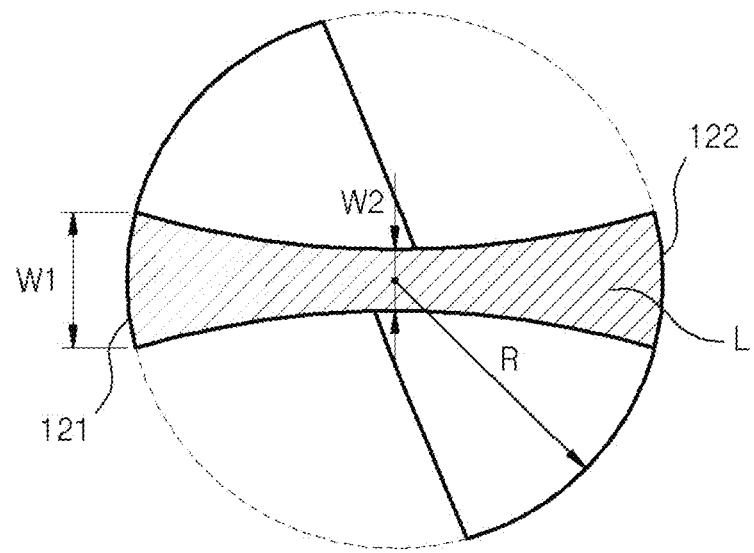
FIG. 4 is a sectional view taken along a line IV-IV of FIG. 2.
Figure 5:
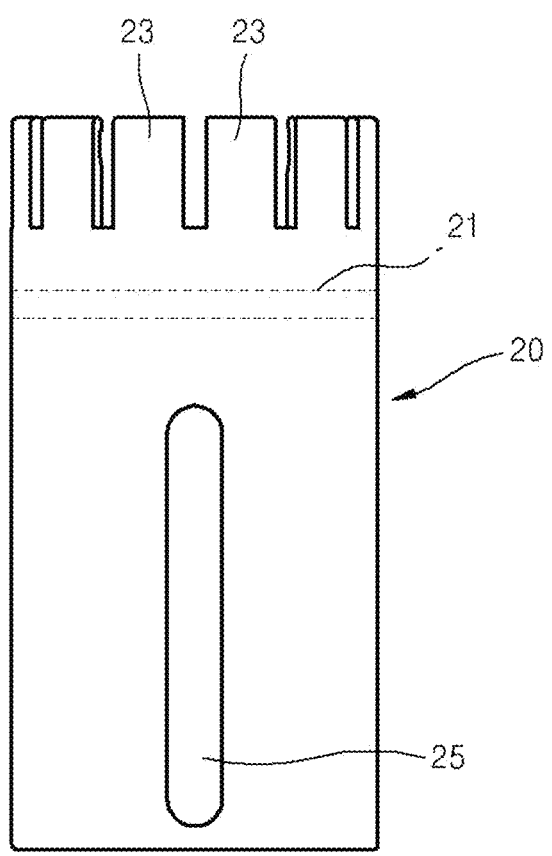
FIG. 5 is a front view of a drill cover employed in the autogenous bone collector shown in FIG. 1.
Figure 6:
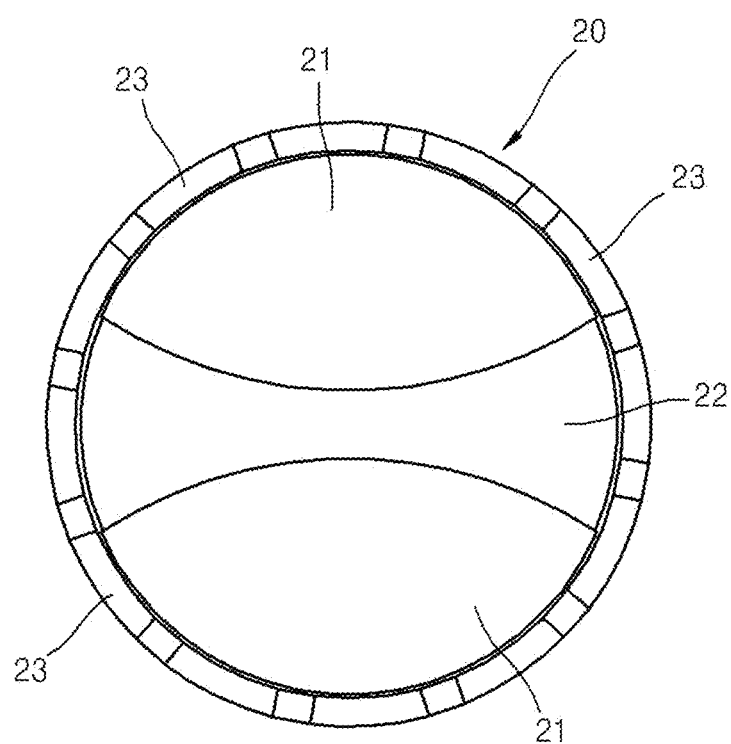
FIG. 6 is a plan view of the drill cover shown in FIG. 5.
Figure 7:
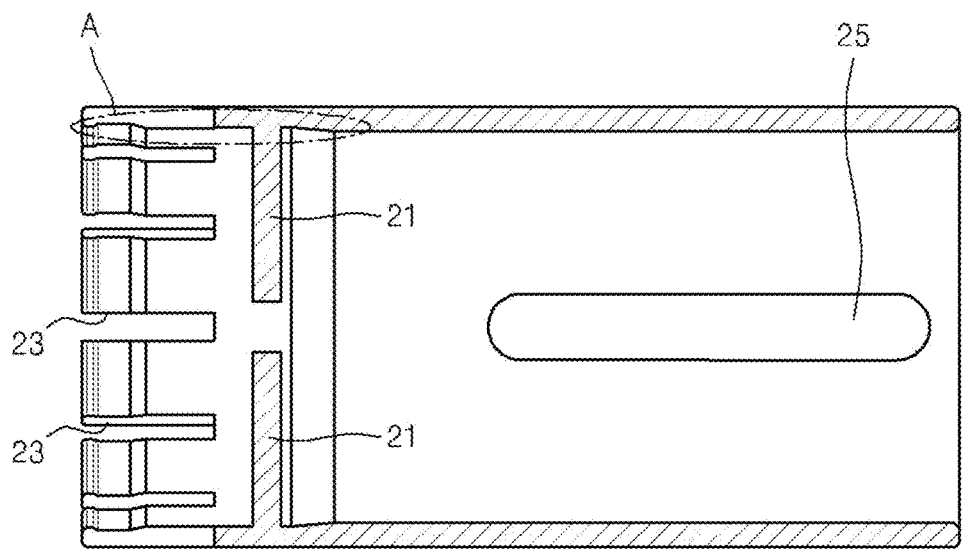
FIG. 7 is a sectional view of the drill cover shown in FIG. 5.
Figure 8:
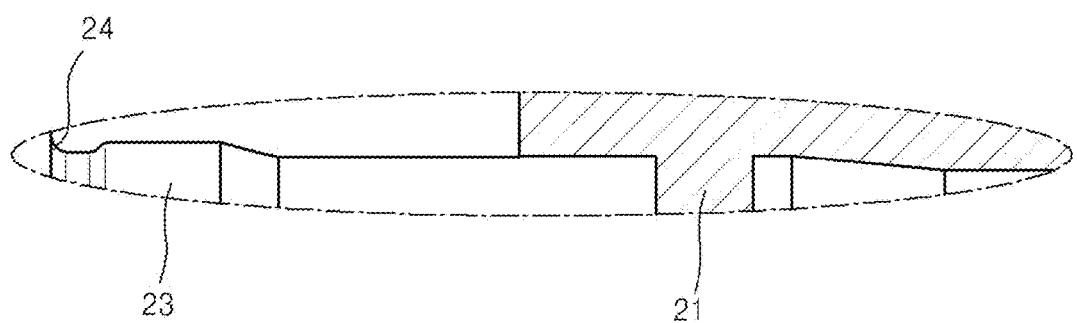
FIG. 8 is a diagram showing a section "A" of FIG. 7 in closer detail.
Figure 9:
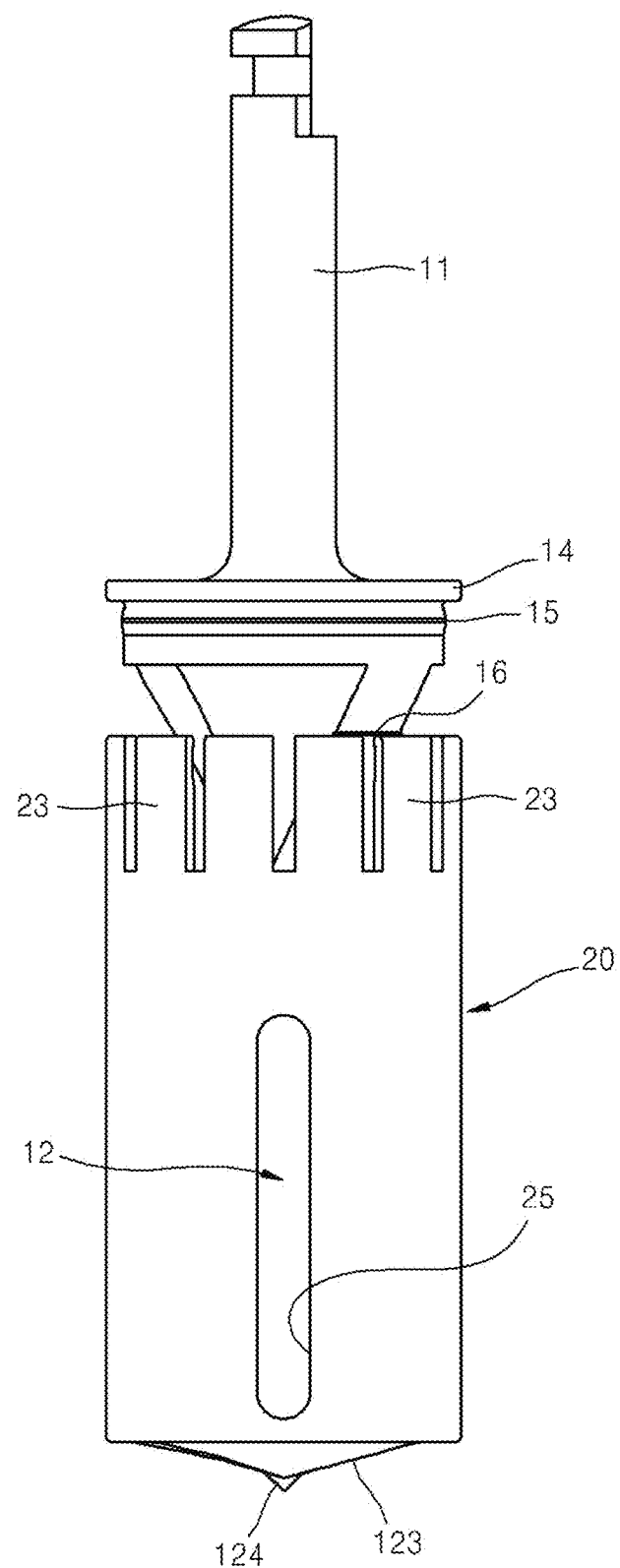
FIG. 9 is a diagram showing primary combination of the drill and the drill cover employed in the autogenous bone collector according to an embodiment of the present invention.
Figure 10:
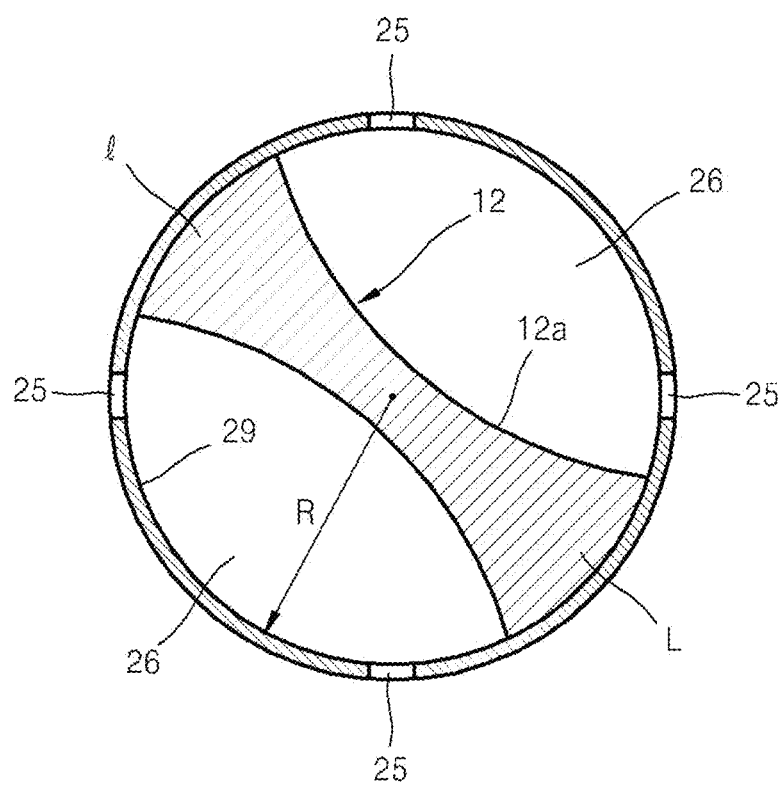
FIG. 10 is a sectional view taken along a line X-X of FIG. 1.

FIG. 1 is a front view of an autogenous bone collector according to an embodiment of the present invention. FIG. 2 is a front view of a drill employed in the autogenous bone collector shown in FIG. 1. FIG. 3 is a bottom view of the drill shown in FIG. 2. FIG. 4 is a sectional view obtained along a line IV-IV of FIG. 2. FIG. 5 is a front view of a drill cover employed in the autogenous bone collector shown in FIG. 1. FIG. 6 is a plan view of the drill cover shown in FIG. 5. FIG. 7 is a sectional view of the drill cover shown in FIG. 5. FIG. 8 is a diagram showing a section "A" of FIG. 7 in closer detail. FIG. 9 is a diagram showing primary combination of the drill and the drill cover. FIG. 10 is a sectional view taken along a line X-X of FIG. 1.

First, referring to FIGS. 1 and 2, a drill 10 according to an embodiment of the present invention includes a shaft unit 11 to be connected to a driving device and a cutting unit 12 which revolves and collects bone particles of a patient. The cross-sectional area L of the cutting unit 12 is from 10% to 40% of an area of a circle having a radius R corresponding to a distance from the center of the cutting unit 12 to the outermost end portion of the cutting unit 12.

If the cross-sectional area L of the cutting unit 12 is smaller than 10% of the area of the circle, strength of the cutting unit 12 is deteriorated. If the cross-sectional area L of the cutting unit 12 is greater than 40% of the area of the circle, a space storage 26 (see FIG. 10) for housing collected bone particles is reduced due to an increase in a space occupied by the cutting unit 12.

The cross-sectional area L of the cutting unit 12 according to the present embodiment is 20% of an area of a circle having the radius R corresponding to a distance from the center of the cutting part 12 to the outermost end portion of the cutting unit 12. In the related art, it is common that cross-sectional area of a cutting unit is formed to exceed 50% of an area of a circle having the radius R corresponding to a distance from the center of the cutting unit to the outermost end portion of the cutting unit.

The drill 10 is provided to collect bone particles of a patient when the drill 10 revolves as driving power is transmitted from a driving device (not shown).

The shaft unit 11 is connected to the driving device, revolves by receiving driving power therefrom, and extends in a direction. Referring to FIG. 2, a riving device is connected to the upper portion of the shaft unit 11, whereas the cutting unit 12 is arranged at the lower portion of the shaft unit 11.

In the present embodiment, the shaft unit 11 and the cutting unit 12 are connected to each other via a connecting unit 13. In other words, the shaft unit 11 is connected to the upper end portion of the connecting unit 13, whereas the cutting unit 12 is connected to the lower end portion of the connecting unit 13.

The cutting unit 12 revolves with the shaft unit 11, cuts into an autogenous bone of a patient, and collects bone particles. The cutting unit 12 extends spirally in the direction in which the shaft unit 11 extends.

Referring to FIG. 2, the cutting unit 12 according to the present embodiment includes a first blade 121 and a second blade 122.

The first and second blades 121 and 122 extend spirally downward from the connecting unit 13, where the first and second blades 121 and 122 extend at a same pitch. Threads formed as the first blade 121 and the second blade 122 spirally extend (portions like screw threads) provide the storage space 26 in which bone particles collected from an autogenous bone are housed.

As shown in FIG. 3, two or more sub-sloped surfaces having different slopes are formed at an end portion of the cutting unit 12. In the present embodiment, the end portion of the cutting unit 12, that is, leading end portions of the first and second blades 121 and 122 are formed to have two-stage sub-sloped surfaces.

In detail, the two-stage sub-sloped surfaces are denoted by the reference numerals 121a, 121b, 122a, and 122b. The sub-sloped surfaces 121a and 121b having different slopes are formed at the leading end portions of the first blade 121, whereas the sub-sloped surfaces 122a and 122b having different slopes are formed at the leading end portions of the second blade 122. The sub-sloped surfaces 121a and 122a have a same slope, whereas the sub-sloped surfaces 121b and 122b have a same slope. The slope of the sub-sloped surfaces 121a and 122a is smaller than that of the sub-sloped surfaces 121b and 122b.

FIG. 4 is a cross-sectional view of the cutting unit 12. The outermost thickness W1 of the first blade 121 or the second blade 122 is greater than thickness W2 of the center portion of the first blade 121 or the second blade 122.

In other words, the first blade 121 and the second blade 122 is manufactured, such that thickness thereof decreases toward the center portion of the cutting unit 12. By forming the first blade 121 and the second blade 122 is manufactured, such that thickness thereof decrease toward the center portion of the cutting unit 12, the storage space 26 for housing bone particles collected from revolutions of the first and second blades 121 and 122 may become larger.

Referring to FIG. 2, the end portion of the cutting unit 12 includes a sloped surface 123, such that the center portion of the cutting unit 12 has a pointed shape. Furthermore, a pointer 124 that protrudes and has a larger slope than the sloped surface 123 is attached to the center portion of the end portion of the cutting unit 12. The pointer 124 is formed as a single body with the cutting unit 12.

When the cutting unit 12 approaches an autogenous bone of a patient, the pointer 124 allows the cutting unit 12 to easily approach the autogenous bone to be contacted.

Furthermore, during revolution of the cutting unit 12, the pointer 124 reduces rocking shaking of the cutting unit 12. In other words, the pointer 124 allows the cutting unit 12 to approach to a precise location for collecting bone particles and reduces rocking of the cutting unit 12 during a surgery.

According to the present embodiment, the drill 10 includes a shoulder 14 and first and second protrusions 15 and 16.

The shoulder 14 protrudes from the outer circumferential surface of the drill 10. In the present embodiment, the shoulder 14 is arranged above the connecting unit 13 and protrudes outward. Movement of a drill cover 20 described below is restricted by the shoulder 14. In detail, when the drill cover 20 moves upward, the drill cover 20 is stopped by the shoulder 14 and movement thereof is restricted.

The first protrusion 15 is arranged below the shoulder 14. In the present embodiment, the first protrusion 15 protrudes along the outer circumferential surface of the connecting unit 13. Hook protrusions 24 (see FIG. 8) of the drill cover 20 described below are stopped by the first protrusion 15.

The second protrusion 16 is formed below the first protrusion 15. In the present embodiment, the second protrusion 16 protrudes along the outer circumferential surface of the connecting unit 13. The second protrusion 16 is also stopped by the hook protrusions 24 of the drill cover 20 described below. In detail, the hook protrusions 24 are stopped by the first protrusion 15 after being stopped by the second protrusion 16. Detailed descriptions thereof will be given below.

Meanwhile, the present invention provides an autogenous bone collector including the drill 10. The autogenous bone collector according to the present embodiment includes the drill 10 and the drill cover 20.

The drill 10 according to the present embodiment is described above, and thus detailed descriptions thereof will be omitted.

The drill cover 20 is attached to the drill 10 and forms the storage space 26 for housing bone particles between the inner circumferential surface 29 of the drill cover 20 and the outer circumferential surface 12a of the cutting surface 1 of the cutting unit 12.

The drill cover 20 is attached to the drill 10, such that the leading end portion of the drill 10 may protrude from the drill cover 20. The drill cover 20 includes a housing portion 22 through which the cutting surface 1 of the cutting unit 12 may pass.

In other words, the housing portion 22 is formed to have a shape corresponding to a shape of the cutting surface 1 of the cutting unit 12. When the drill cover 20 is attached to the drill 10, the cutting unit 12 is inserted to the housing portion 22.

In detail, the drill cover 20 is arranged outside the cutting unit 12. The drill cover 20 houses the cutting unit 12. Length of the drill cover 20 is smaller than a distance from the shoulder 14 to the end portion of the cutting unit 12.

Therefore, as shown in FIG. 1, when the upper end of the drill cover 20 contacts the shoulder 14 of the connecting unit 13, the cutting unit 12 protrudes out of the drill cover 20.

In other words, when the cutting unit 12 revolves, cuts into an autogenous bone of a patient, and collects bone particles, the cutting unit 12 protrudes from the bottom of the drill cover 20.

The drill cover 20 includes a partitioning wall 21, protruding fingers 23, and a long hole 25.

Referring to FIG. 6, the partitioning wall 21 protrudes from the inner circumferential surface of the cutting unit 12 toward the center portion of the cutting unit 12 and extends to form the housing portion 22 having a shape corresponding to the cross-sectional shape of the cutting unit 12.

In detail, the partitioning wall 21 extend in a direction in which two walls approach toward each other from the inner circumferential surface of the drill cover 20 and the housing portion 22 in which the cutting unit 12 is housed is formed between the two walls.

The partitioning wall 21 helps collection of bone particles by scraping bone particles filed at the cutting unit 12 when the drill cover 20 is detached from the cutting unit 12 after the bone particles are collected while the drill cover 20 is being attached to the cutting unit 12.

Referring to FIG. 5, the protruding fingers 23 are formed at the upper portion of the drill cover 20. In the present embodiment, the protruding fingers 23 protrude from the upper end of the drill cover 20 to be apart from each other by a constant interval in the circumferential direction.

Therefore, the plurality of protruding fingers 23 are arranged at the upper end of the drill cover 20. However, a number of the protruding fingers 23 and an interval therebetween may vary. In other words, the protruding fingers 23 may be arranged to be apart from each other by different intervals.

Referring to FIGS. 7 and 8, the hook protrusions 24 that are bent inward are arranged at the upper ends of protruding fingers 23. The hook protrusions 24 are primarily stopped by the second protrusion 16 when the drill cover 20 is attached to the cutting unit 12 and are secondarily stopped by the first protrusion 15 as the drill cover 20 moves upward when the cutting unit 12 revolves.

Since the plurality of protruding fingers 23 are arranged to be apart from each other, the protruding fingers 23 are elastically-deformed slightly when the hook protrusions 24 are stopped by the first and second protrusions 15 and 16, such that the drill cover 20 are easily attached to the first and second protrusions 15 and 16.

The long hole 25 is arranged to inject water between the drill cover 20 and the cutting unit 12 to cool off heat generated while the cutting unit 12 is revolving and collecting an autogenous bone. The long hole 25 is formed to have a long shape extending in a vertical direction and penetrates through the outer and inner circumferential surfaces of the drill cover 20.

According to the present embodiment, the long hole 25 extends upward from a point close to the bottom end of the drill cover 20. The upper end of the long hole 25 is located below the partitioning wall 21. In other words, a first end of the long hole 25 is close to the bottom end of the drill cover 20, and the long hole 25 extends upward, such that a second end (the upper end) of the long hole 25 is located below the partitioning wall 21.

Hereinafter, operation of an autogenous bone collector having the configuration described above will be described in detail.

Referring to FIG. 8, an end portion of the cutting unit 12 is brought close to the upper end of the drill cover 20 (the protruding fingers 23) and the cutting unit 12 is attached to the drill cover 20. Since the cutting unit 12 may go through the housing portion 22 formed by the partitioning wall 21, the hook protrusions 24 are moved to a location at which the hook protrusions 24 are stopped by the second protrusion 16 by revolving the cutting unit 12 and the drill cover 20 relatively with each other. During the process, the cutting unit 12 is primarily combined with the drill cover 20.

Next, when the shaft unit 11 is connected to the driving device and the shaft 11 is revolved by applying driving power thereto, the drill cover 20 moves upward along the threads formed by the first and second blades 121 and 122.

Here, as shown in FIG. 1, the drill cover 20 moves to a location at which the drill cover 20 is stopped by the shoulder 14, and the hook protrusions 24 is stopped by the first protrusion 15. Therefore, relative locations of the cutting unit 12 and the drill cover 20 are set.

Next, the pointer 124 of the cutting unit 12 is located on an autogenous bone of a patient. Since the pointer 124 has a greater slope than the sloped surface 123 of the cutting unit 12, the pointer 124 may be located precisely on location of the autogenous bone from which bone particles are to be collected.

Next, bone particles are collected by revolving the shaft unit 11. During the process, length of a portion of the cutting unit 12 which may protrude below the drill cover 20 is limited, the length of the portion of the cutting unit 12 cutting into the autogenous bone may be constantly maintained, and thus the length of the portion of the cutting unit 12 cutting into the autogenous bone may be controlled.

In other words, the length of the portion of the cutting unit 12 protruding below the drill cover 20 may be adjusted by adjusting length of the drill cover 20, and thus the length of the portion of the cutting unit 12 cutting into an autogenous bone may be controlled by manufacturing the drill cover 20 having a desired length. While the cutting unit 12 is revolving, collected bone particles are housed in the storage space 26.

When collection of bone particles are completed, the drill cover 20 is detached from the cutting unit 12. The drill cover 20 is detached by revolving the drill cover 20 relatively with respect to the cutting unit 12. During the process, the partitioning wall 21 scrapes bone particles filed at the cutting unit 12.

In other words, bone particles between the first and second blades 121 and 122 are scraped by the partitioning wall 21 and fall in the drill cover 20. Therefore, the bone particles are automatically removed from the cutting unit 12.

Furthermore, water is injected via the long hole 25 during a surgery, and the length thereof is always constant. Therefore, a constant amount of water is stably supplied during a surgery to prevent bone heating.

As described above, the autogenous bone collector according to an embodiment of the present invention maintains a constant cutting depth of the cutting unit 12 cutting into an autogenous bone of a patient. Furthermore, bone particles collected by the cutting unit 12 are housed in the storage space 26 that is larger than a storage space provided in the related art, and thus a relatively large number of bone particles may be collected.

Furthermore, bone particles filed at the cutting unit 12 may be scraped easily. Therefore, stability of a surgery may be improved and a period of time elapsed for the surgery may be significantly reduced.

Figure 19:
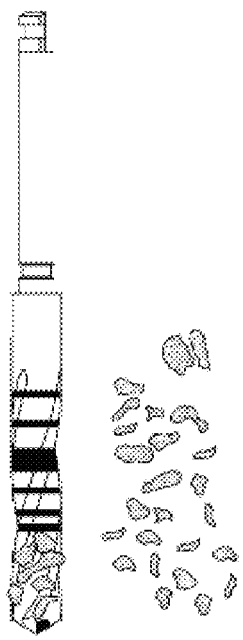
FIG. 19 is a photograph of bone particles collected by using an autogenous bone collector in the related art.
Figure 20:
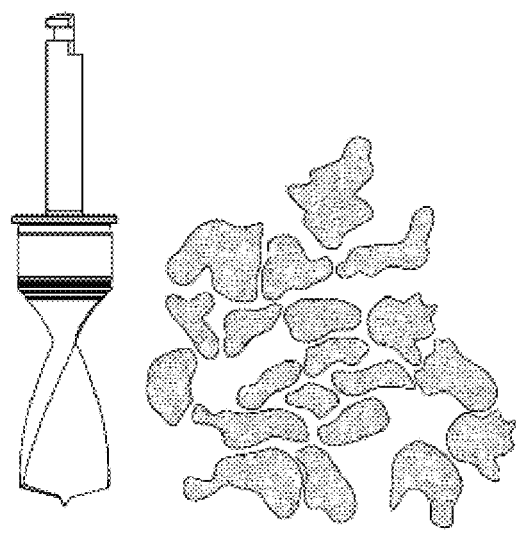
FIG. 20 is a photograph of bone particles collected by using an autogenous bone collector according to an embodiment of the present invention.

Furthermore, the drill 10 according to an embodiment of the present invention includes two or more sub-sloped surfaces having different slopes at its leading end portion, and thus cutting efficiency of the drill 10 is significantly improved. Detailed descriptions thereof will be given with reference to FIGS. 19 and 20. FIGS. 19 and 20 are photographs respectively showing bone particles collected by an autogenous bone collector according to an embodiment of the present invention and bone particles collected by an autogenous bone collector in the related art.

Referring to FIGS. 19 and 20, sizes of bone particles collected by the autogenous bone collector according to an embodiment of the present invention are significantly larger than those collected by the autogenous bone collector in the related art.

Therefore, improved cutting efficiency enables collection of larger bone particles, and such large bone particles are suitable for an implant surgery.

Meanwhile, a drill, a drill cover, and an autogenous bone collector employing the same, according to another embodiment of the present invention will be described below with reference to FIGS. 11 through 18.

Figure 11:
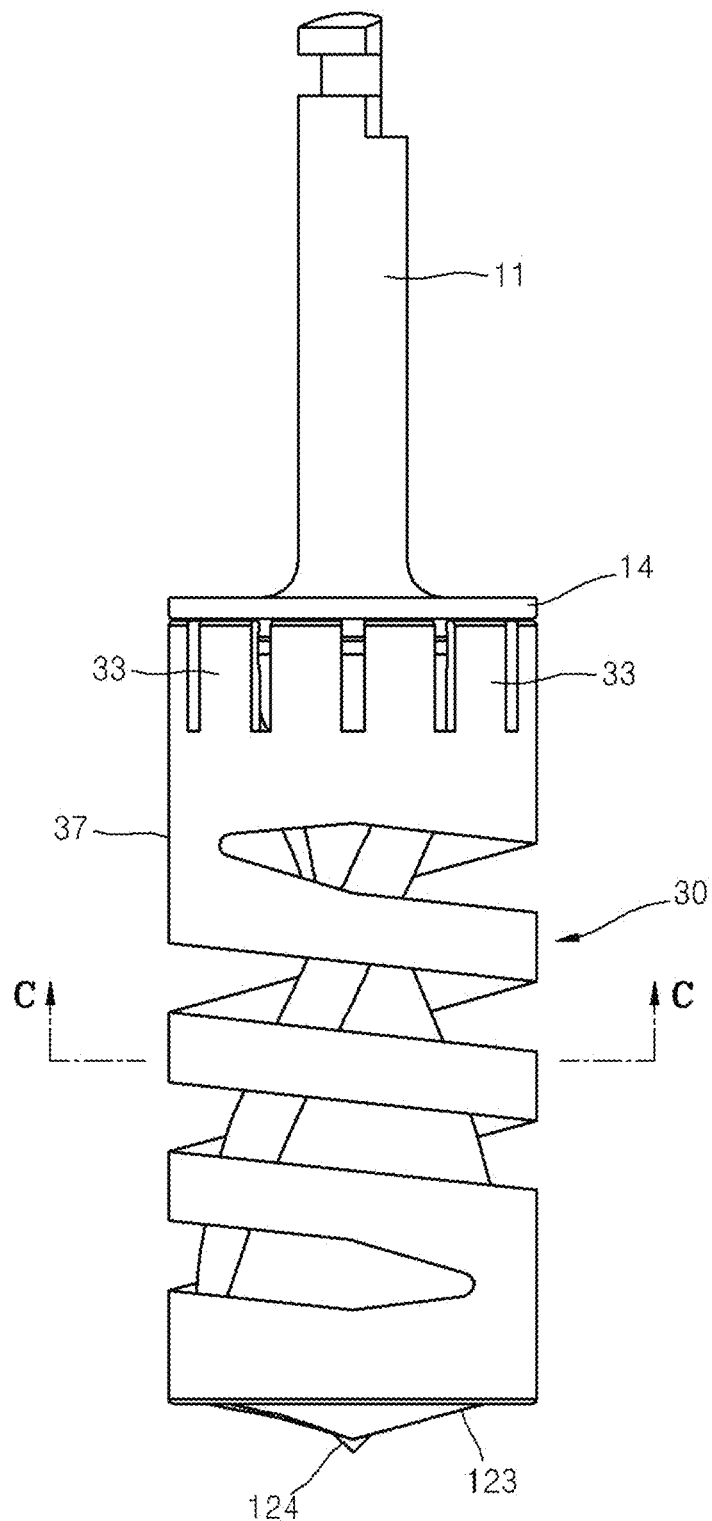
FIG. 11 is a front view of an autogenous bone collector according to another embodiment of the present invention.
Figure 12:
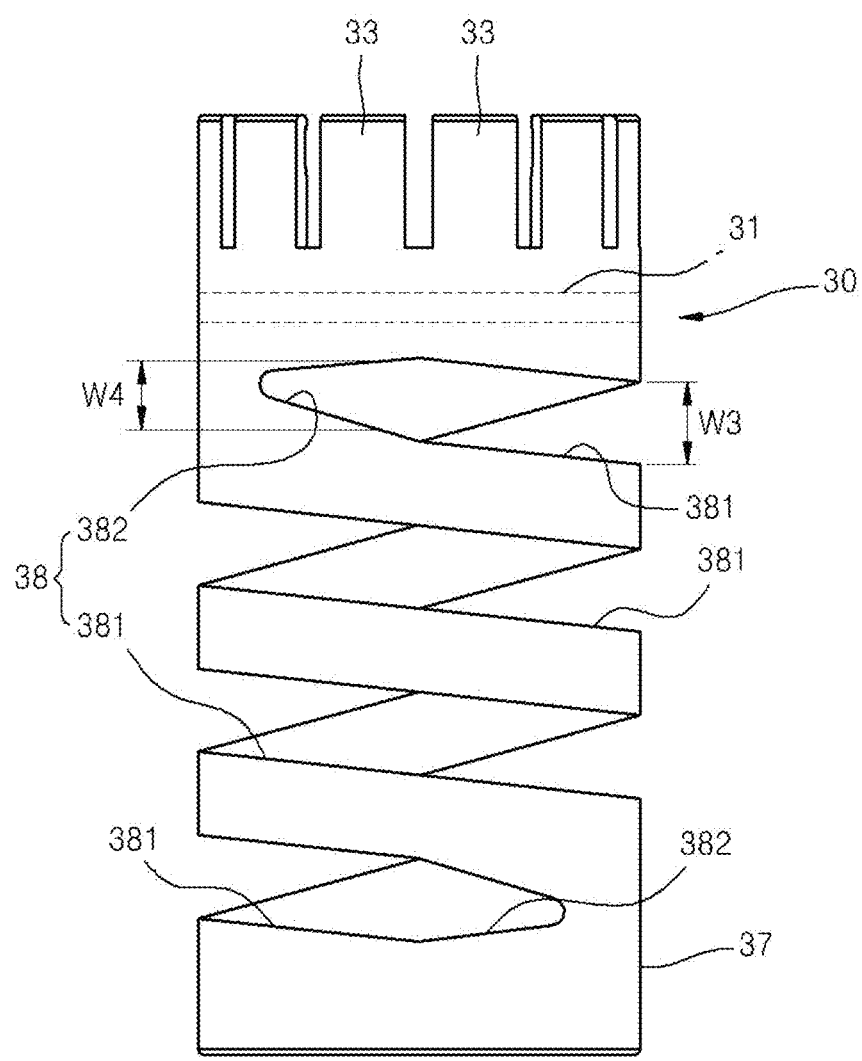
FIG. 12 is a front view of a drill cover employed in the autogenous bone collector shown in FIG. 11.
Figure 13:
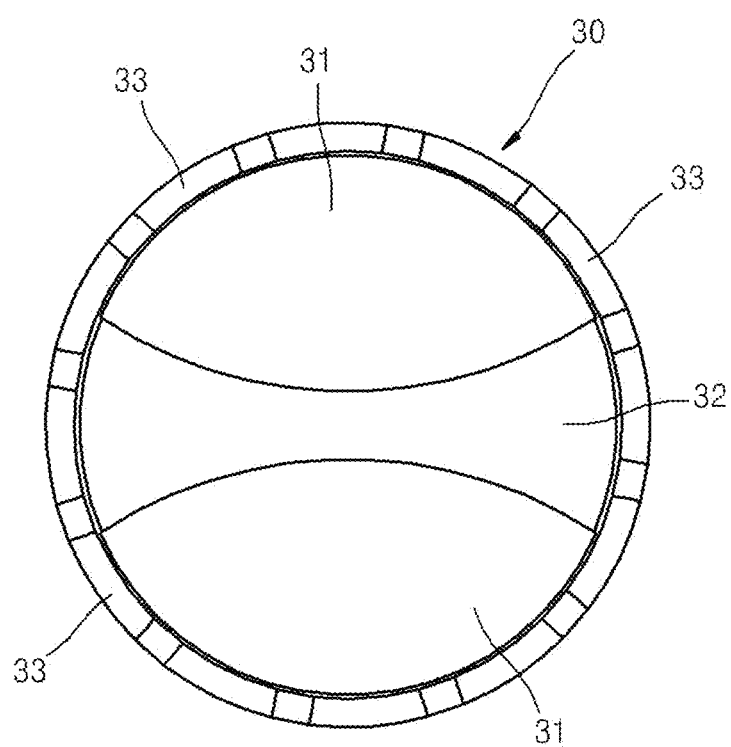
FIG. 13 is a plan view of the drill cover shown in FIG. 12.
Figure 14:
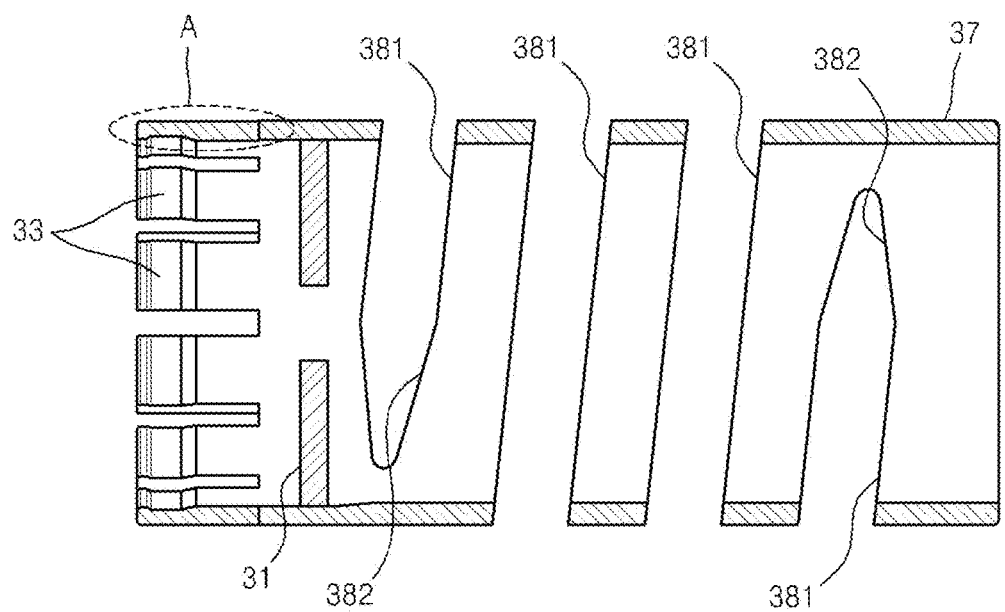
FIG. 14 is a sectional view of the drill cover shown in FIG. 12.
Figure 15:
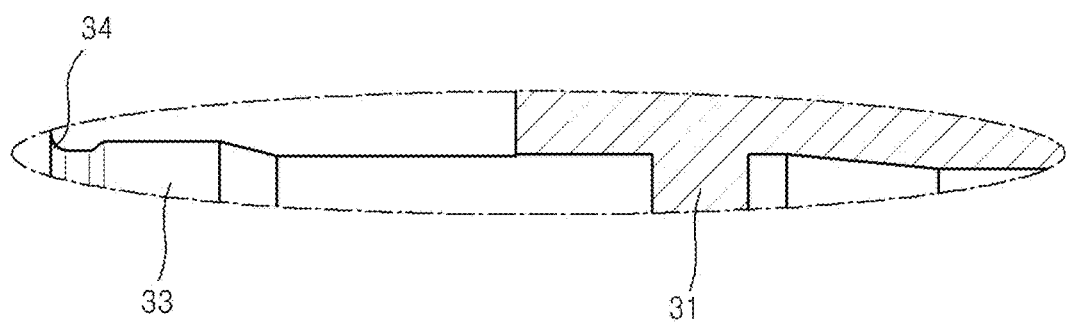
FIG. 15 is a diagram showing a section "A" of FIG. 14 in closer detail.
Figure 16:
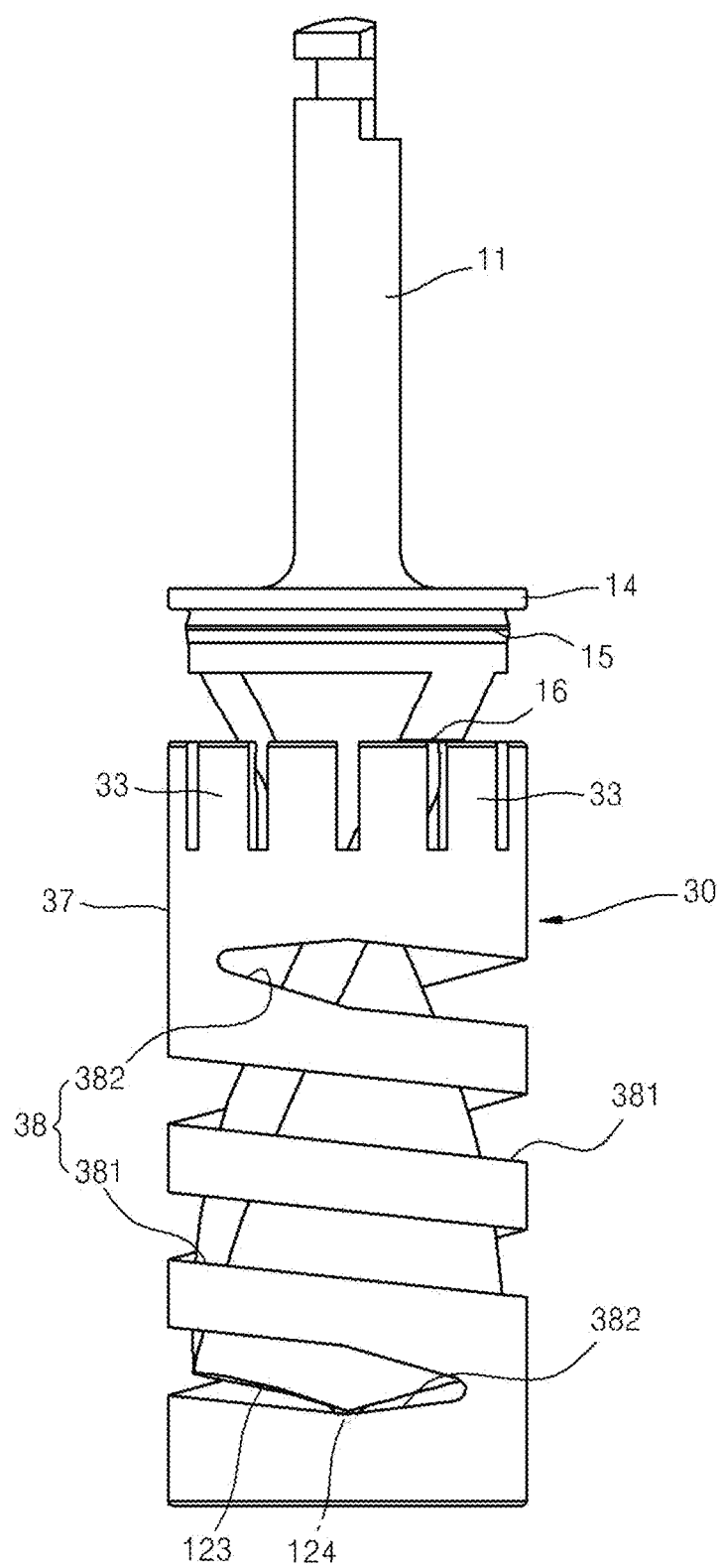
FIG. 16 is a diagram showing primary combination of the drill and the drill cover employed in the autogenous bone collector according to another embodiment of the present invention.
Figure 17:
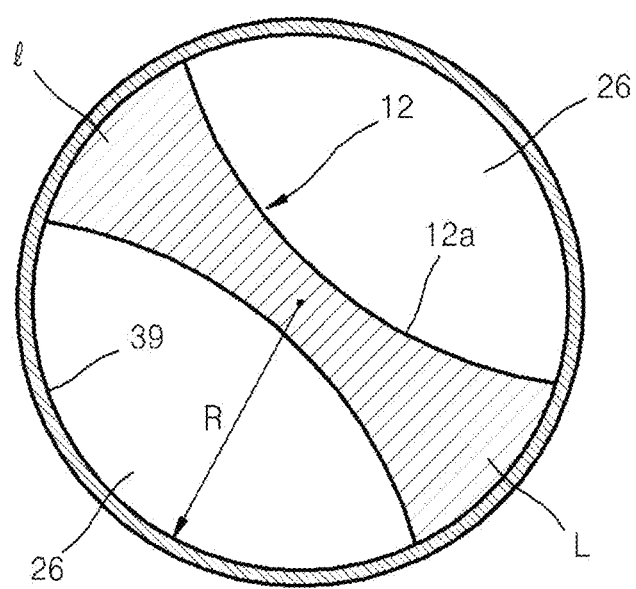
FIG. 17 is a sectional view taken along a line C-C of FIG. 11.

FIG. 11 is a front view of an autogenous bone collector according to another embodiment of the present invention. FIG. 12 is a front view of a drill cover employed by the autogenous bone collector shown in FIG. 11. FIG. 13 is a plan view of the drill cover shown in FIG. 12. FIG. 14 is a sectional view of the drill cover shown in FIG. 12. FIG. 15 is a diagram showing the section "A" of FIG. 7 in closer detail. FIG. 16 is a diagram showing primary combination of the drill and the drill cover. FIG. 17 is a sectional view obtained along a line C-C of FIG. 11.

First, referring to FIGS. 11 and 12, a drill cover 30 according to the present embodiment is attached to the drill 10 having the cutting unit 12 which revolves and collects bone particles of a patient.

The drill cover 30 forms the storage space 26 for housing bone particles between the inner circumferential surface 39 of the drill cover 30 and the cutting surface 1 of the cutting unit 12 (refer to FIG. 17). In other words, the drill cover 30 is arranged for bone particles collected by the drill 10 to be collected within the storage space 26 without popping out of the drill cover.

The drill cover 30 includes a main body 37 and a cut-open portion 38.

The top and the bottom of the main body 37 are opened, and the main body 37 is attached to the exterior of the cutting unit 12. The drill 10 goes through the main body 37 and is combined therewith.

The main body 37 is formed of titanium nitride (TiN) or stainless steel. Since the main body 37 is formed of TiN or stainless steel, the main body 37 may be repeatedly used and has improved durability. During sterilization of the main body 37, structure of the main body 37 is unchanged even at high temperatures. Therefore, the main body 37 may be continuously used.

An end portion of the main body 37 is located close to an end portion of the cutting unit 12. In detail, the end portion of the main body 37 is located slightly above the end portion of the cutting unit 12. In other words, as shown in FIG. 11, when the drill cover 30 is attached to the drill 10, a portion of the end portion of the cutting unit 12 slightly protrudes out of the end portion of the drill cover 30.

By locating the end portion of the main body 37 close to the end portion of the cutting unit 12, bone particles collected by revolution of the cutting unit 12 during the early state of the revolution of the cutting unit 12 are prevented from being popped out of the drill cover 30.

The cut-open portion 38 is arranged to be compressible in a direction in which the upper portion and the lower portion of the main body 37 approach to each other. The cut-open portion 38 is spiral cuts formed in the main body 37.

The cut-open portion 38 extends downward while rotating to the left or the right in a spiral shape. Therefore, since the cut-open portion 38 is formed by spirally cutting the outer circumferential surface of the main body 37, the drill cover 30 has an overall spring-like structure.

Referring to FIG. 12, the cut-open portion 38 is formed at a constant pitch. Furthermore, although not shown, the cut-open portion 38 may be formed at varying pitches. In other words, the cut-open portion 38 may be formed at inconstant pitches. Force necessary for compressing the drill cover 30 may be adjusted by adjusting the pitch of the cut-open portion 38. In other words, tension of the drill cover 30 may be adjusted.

For example, force necessary for compressing the drill cover 30 may be reduced by forming the upper portion and the lower portion of the cut-open portion 38 at a same pitch and forming the middle portion of the cut-open portion 38 at a pitch shorter than the pitches of the upper portion and the lower portion of the cut-open portion 38. The pitch of the cut-open portion may be manufactured in various forms.

According to the present embodiment, the cut-open portion 38 includes a first cut-open portion 381 and a second cut-open portion 382.

The first cut-open portion 381 has a constant first cut-open width W3. The second cut-open portion 382 has a second cut-open width W4 smaller than the first cut-open width W3. Of course, the cut-open portion 38 may also be formed to have a constant width.

The second cut-open portion 382 extend from two opposite ends of the first cut-open portion 381, where width of the second cut-open portion 382 gradually decreases toward the end portions thereof.

When the drill cover 30 is compressed, widths of the first and second cut-open portions 381 and 382 decrease. At this point, the tapered shape of the second cut-open portion 382 induces easy compression at the end portion of the second cut-open portion 382 to prevent collected bone particles from popping out of the drill cover 30.

The drill cover 30 further includes partitioning wall 31 and protruding fingers 33.

Referring to FIG. 13, the partitioning wall 31 extends from the inner circumferential surface of the main body 37. The partitioning wall 31 includes a housing portion 32 through which the cutting surface 1 of the cutting unit 17 may pass.

In detail, the partitioning wall 31 extend in a direction in which two walls approach toward each other from the inner circumferential surface of the main body 37 and the housing portion 32 in which the cutting unit 12 is housed is formed between the two walls.

In other words, the housing portion 32 is formed to have a shape corresponding to a shape of the cutting surface 1 of the cutting unit 12. When the drill cover 30 is attached to the drill 10, the cutting unit 12 is inserted to the housing portion 32.

The partitioning wall 31 helps collection of bone particles by scraping bone particles attached to the outer circumferential surface of the cutting unit 12 when the drill cover 30 is detached from the cutting unit 12 after the bone particles are collected while the drill cover 30 is being attached to the cutting unit 12.

Referring to FIGS. 12 and 13, the protruding fingers 33 are formed at the upper portion of the drill cover 30. In the present embodiment, the protruding fingers 33 protrude upward from the upper end of the drill cover 20 to be apart from each other by a constant interval in the circumferential direction.

Therefore, the plurality of protruding fingers 33 are arranged at the upper end of the drill cover 30. However, a number of the protruding fingers 33 and an interval therebetween may vary. In other words, the protruding fingers 33 may be arranged to be apart from each other by different intervals.

Referring to FIGS. 14 and 15, the hook protrusions 34 that are bent inward are arranged at the upper ends of protruding fingers 23. The hook protrusions 34 are primarily stopped by the second protrusion 16 when the drill cover 30 is attached to the cutting unit 12 and are secondarily stopped by the first protrusion 15 when the drill cover 30 moves further upward.

Furthermore, according to another embodiment of the present invention, an autogenous bone collector employing the drill cover 30 described above is provided. The autogenous bone collector includes the drill 10 having the shaft unit 11 to be connected to a driving device and a cutting unit 12 which revolves and collects bone particles of a patient and the drill cover 30 having the main body 37 that has the top and the bottom opened and is attached to the exterior of the cutting unit 12, and the cut-open portion 38 that is arranged to be compressible in a direction in which the upper portion and the lower portion of the main body 37 approach to each other.

Since the drill cover 30 constituting the autogenous bone collector is described above, detailed description thereof will be omitted below.

Furthermore, the drill 10 employed in the present embodiment is same as the drill according to the above embodiment (refer to FIG. 2), and thus detailed descriptions thereof will be omitted.

Figure 18:
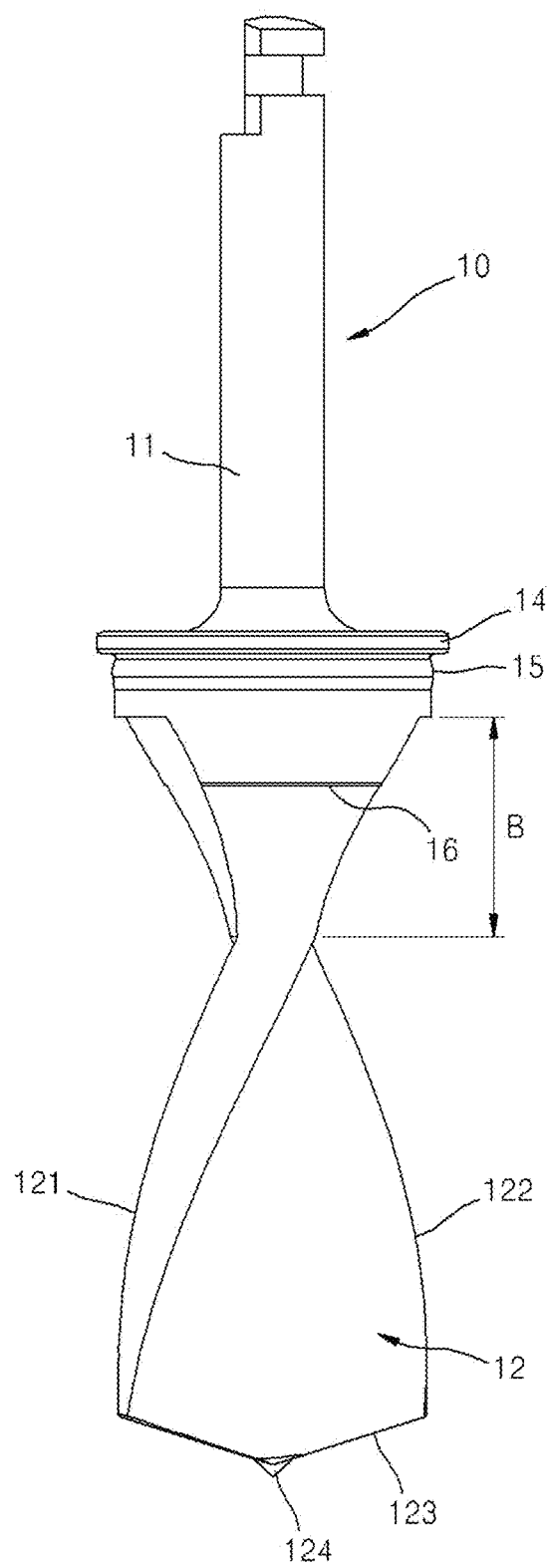
FIG. 18 is a front view of a drill according to another embodiment of the present invention.

Furthermore, the cutting unit 12 is formed to have the constant outermost width. Meanwhile, FIG. 18 shows an example of modifications of the drill 10. As shown in FIG. 18, the cutting unit 12 may be formed, such that outermost width of the cutting unit 12 increases toward the shaft unit 11 (section B of FIG. 18).

Hereinafter, effects of an autogenous bone collector employing the drill cover 30 will be described in detail.

First, referring to FIG. 16, an end portion of the cutting unit 12 is brought close is to the upper end of the drill cover 30 (the protruding fingers 33) and the cutting unit 12 is attached to the drill cover 30. Since the cutting unit 12 may go through the housing portion 32 formed by the partitioning wall 31, the hook protrusions 34 are moved to a location at which the hook protrusions 34 are stopped by the second protrusion 16 by revolving the cutting unit 12 and the drill cover 30 relatively with each other. During the process, the cutting unit 12 is primarily combined with the drill cover 30.

Next, when the shaft unit 11 is further revolved, the drill cover 30 moves upward along the threads formed by the first and second blades 121 and 122.

Here, as shown in FIG. 10, the drill cover 30 moves to a location at which the drill cover 30 is stopped by the shoulder 14, and the hook protrusions 34 is stopped by the first protrusion 15. Therefore, relative locations of the cutting unit 12 and the drill cover 30 are set. The protruding fingers 33 are elastically-deformed slightly when the hook protrusions 34 are stopped by the first and second protrusions 15 and 16, such that the drill cover 30 are easily attached to the drill 10.

Next, the pointer 124 of the cutting unit 12 is located on an autogenous bone of a patient. Since the pointer 124 has a greater slope than the sloped surface 123 of the cutting unit 12, the pointer 124 may be located precisely on location of the autogenous bone from which bone particles are to be collected.

The driving device is connected to the shaft unit 11 and the shaft unit 11 is revolved by applying driving power thereto. The cutting unit 12 cuts into an autogenous bone while pushing the drill 10 toward the autogenous bone. During the early stage of the revolution of the cutting unit 12, the lower portion of the main body 37 is located close to the autogenous bone. Therefore, bone particles collected during the early stage of the revolution of the cutting unit 12 are prevented from popping out of the drill cover 30.

When the drill 10 is pushed toward the autogenous bone, the main body 37 of the drill cover 30 is compressed. During the process, an end portion of the cutting unit 12 gradually protrudes below the main body 37.

The end portion of the cutting unit 12 continues to protrude until the main body 37 is fully compressed. In other words, length of a portion of the cutting unit 12 which may protrude below the drill cover 30 is limited. Therefore, the length of the portion of the cutting unit 12 cutting into the autogenous bone may be constantly maintained, and thus the length of the portion of the cutting unit 12 cutting into the autogenous bone may be controlled.

In other words, the length of the portion of the cutting unit 12 protruding below the drill cover 30 may be adjusted by adjusting length of the main body 37 of the drill cover 30. While the cutting unit 12 is revolving, collected bone particles are housed in the storage space 26.

When collection of bone particles are completed, the drill cover 30 is detached from the cutting unit 12. The drill cover 30 is detached by revolving the drill cover 30 relatively with respect to the cutting unit 12. During the process, the partitioning wall 31 scrapes bone particles filed at the cutting unit 12.

In other words, bone particles between the first and second blades 121 and 122 are scraped by the partitioning wall 31 and fall in the drill cover 30. Therefore, the bone particles are automatically removed from the cutting unit 12.

As described above, since the lower end portion of the drill cover 30 according to the present embodiment may be located close to an autogenous bone, bone particles collected during the early stage of the revolution of the cutting unit 12 are prevented from popping out of the drill cover 30.

Furthermore, since the drill cover 30 is manufactured to have a spring-like shape, length of the portion of the cutting unit 12 cutting into an autogenous bone of a patient may be maintained constant, thereby improving stability of a surgery.

Furthermore, since the drill cover 30 is formed of TiN or stainless steel, the drill cover 30 has an improved durability and may be repeatedly used. Furthermore, during a high-temperature sterilization, shape of the drill cover 30 may be unchanged.

Furthermore, since the drill cover 30 includes the partitioning wall 31, bone particles attached to the outer circumferential surface of the cutting unit 12 may be scraped easily. Therefore, a period of time elapsed for the surgery may be significantly reduced.

Meanwhile, an autogenous bone collector employing a drill cover according to an embodiment of the present invention may collect larger number of bone particles, because bone particles collected by the cutting unit 12 are housed in a storage space larger than that in the related art.

Furthermore, the drill 10 employed in the embodiments of the present invention includes two or more sub-sloped surfaces having different slopes at its leading end portion, and thus cutting efficiency of the drill 10 is significantly improved. Detailed descriptions thereof will be given with reference to FIGS. 19 and 20. FIGS. 19 and 20 are photographs respectively showing bone particles collected by an autogenous bone collector according to an embodiment of the present invention and bone particles collected by an autogenous bone collector in the related art.

Referring to FIGS. 19 and 20, sizes of bone particles collected by the autogenous bone collector according to an embodiment of the present invention are significantly larger than those collected by the autogenous bone collector in the related art. Therefore, improved cutting efficiency enables collection of larger bone particles, and such large bone particles are suitable for an implant surgery.

According to embodiments of the present invention as described above, there are provided a drill and a drill cover for collecting bone particles during an implant surgery, improving a capacity of housing bone particles, easily separating bone particles from a cutting unit, controlling depth of the cutting unit penetrating into an autogenous bone, and for housing bone particles collected by the drill within the drill cover without popping out of the drill cover, and an autogenous bone collector using the same.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An autogenous bone collector comprising:
    a drill having a shaft unit connected to a driving device and a cutting unit which revolves and collects bone particles of a patient;
    wherein a cross-sectional area at a middle portion of the cutting unit is from 10% to 40% of an area of a circle having a radius corresponding to a distance from the center of the cutting unit to an outermost end portion of the cutting unit; and
    a drill cover attached to an exterior surface of the cutting unit and comprising a hollow, tubular main body having an upper portion with an open top end, a lower portion with an open bottom end, and a cut-open portion between the upper and lower portions, the cut-open portion including spiral cuts forming a continuous spiral void, wherein the main body is compressible in a longitudinal direction defined between the top and bottom ends such that when sufficient force is applied, the upper portion and the lower portion of the main body approach each other and a width of the spiral void decreases bringing opposing surfaces adjacent the spiral void closer together.

2. The autogenous bone collector of claim 1, wherein the spiral void is formed at a constant pitch.

3. The autogenous bone collector of claim 1, wherein spiral void is formed at varying pitches.

4. The autogenous bone collector of any one of claims 1, 2, and 3, wherein the width of the spiral void portion is constant.

5. The autogenous bone collector of any one of claims 1, 2, and 3, wherein the cut-open portion comprises:
    a first cut-open portion having a constant first cut-open width; and
    a second cut-open portion having a second cut-open width smaller than the first cut-open width.

6. The autogenous bone collector of claim 5, wherein the second cut-open portion extends from two opposite ends of the first cut-open portion, and the width of the second cut-open portion gradually decreases toward an end portion thereof.

7. The autogenous bone collector of claim 1, wherein the spiral void extends downward while rotating the main body to the left or the right.

8. The autogenous bone collector of claim 1, comprising protruding fingers formed at the upper end of the drill cover such that they are spaced apart from each other by a constant interval in a circumferential direction.

9. The autogenous bone collector of claim 8, wherein each protruding finger includes a lip on an inner surface arranged at the upper end of the main body.

10. The autogenous bone collector of claim 1, wherein the main body is formed of titanium or stainless steel.

11. The autogenous bone collector of claim 1, wherein the cutting unit comprises a shoulder protruding from the outer circumferential surface of the drill, wherein movement of the drill cover is restricted by the shoulder, and wherein a protrusion is formed below the shoulder.

12. The autogenous bone collector of claim 1, wherein the cutting unit comprises:
    a first blade, which spirally extends; and
    a second blade, which spirally extends at a same pitch as the first blade.

13. The autogenous bone collector of claim 1, wherein the outermost end portion of the cutting unit comprises two or more sloped surfaces adjacent to a first blade and a second blade of the cutting unit, the two or more sloped surfaces having different slopes from the first blade and the second blade.

14. The autogenous bone collector of claim 1, wherein the cutting unit comprises a pointer that protrudes from a center portion of the outermost end portion of the cutting unit.

15. The autogenous bone collector of claim 1, wherein a thickness of the cutting unit is constant or increases toward the shaft unit.

* * * * *